United States Patent [19]

Wood, Jr.

[11] Patent Number: 4,962,092

[45] Date of Patent: Oct. 9, 1990

[54] COMPOSITIONS FOR TREATING DUODENAL ULCERS

[75] Inventor: Frederick E. Wood, Jr., Maineville, Ohio

[73] Assignee: The Procter & Gamble Company, Cincinnati, Ohio

[21] Appl. No.: 361,890

[22] Filed: Jun. 6, 1989

Related U.S. Application Data

[63] Continuation of Ser. No. 47,844, May 6, 1987, abandoned.

[51] Int. Cl.$^5$ .................. A61K 31/70; A61K 9/00
[52] U.S. Cl. ................... 514/23; 514/53; 514/926
[58] Field of Search .............. 514/926, 925, 927, 53, 514/23

[56] References Cited

U.S. PATENT DOCUMENTS

| | | | |
|---|---|---|---|
| 1,656,474 | 1/1928 | Dubin | 514/547 |
| 2,893,990 | 7/1959 | Hass et al. | 536/119 |
| 2,962,419 | 11/1960 | Minich | 424/122 |
| 3,158,490 | 11/1964 | Baur et al. | 426/612 |
| 3,160,565 | 12/1964 | Duell | 424/147 |
| 3,600,186 | 8/1971 | Mattson et al. | 426/611 |
| 3,954,976 | 5/1976 | Mattson et al. | 514/23 |
| 4,005,196 | 1/1977 | Jandacek | 426/658 |
| 4,029,773 | 6/1977 | Beigler et al. | 514/926 |
| 4,241,054 | 12/1980 | Volpenhein et al. | 514/42 |
| 4,264,583 | 4/1981 | Jandacek | 514/182 |

OTHER PUBLICATIONS

Procter & Gamble Food Additive Petition on Olestra, FDA Docket No. 87F-01791, pp. 25, 91, 92 of vol. 1, Section A, 6/23/87.

USSN 146,648 (Bernhardt), filed 1/21/88 (CIP of 022,190, filed 3/15/89), and 831,379, filed 2/20/86.

*Primary Examiner*—Ronald W. Griffin
*Attorney, Agent, or Firm*—Ronald L. Hemingway; Julius P. Filcik; Richard C. Witte

[57] ABSTRACT

Anti-anal leakage agents are used in combination with vitamin-fortified liquid fatty acid polyester compositions to provide pharmaceutical and food compositions for treating duodenal ulcers while avoiding undesired anal leakage of the polyesters.

24 Claims, No Drawings

COMPOSITIONS FOR TREATING DUODENAL ULCERS

This is a continuation of application Ser. No. 047,844, filed on May 6, 1987, abandoned.

FIELD OF THE INVENTION

The present invention relates to certain edible, but non-absorbable and non-digestible, polyesters which can be used as pharmaceutical compositions for treating and alleviating duodenal ulcers.

BACKGROUND OF THE INVENTION

A variety of dietary and drug regimens have been suggested for alleviating or preventing duodenal ulcers. These include special diets and drugs for alleviating pain and other symptoms.

In the present invention, non-absorbable, non-digestible polyesters of sugars (or sugar alcohols) are used as fat substitutes in foods and, conveniently, in unit dose forms as therapeutic compositions. The polyesters herein are fat-like in their physical properties and are excellent fat substitutes for use in low-calorie foods and diets.

The polyesters herein can be used in combination with fat-soluble vitamins so as to supply the body's requirement therefor. The polyesters herein interfere with the body's absorption of cholesterol and thereby provide a means for treating hypercholesterolemia, as well as ulcer treatment. The polyesters can potentially interfere with the body's absorption of fat-soluble vitamins, but this problem is overcome by fortification with vitamins. It has also been determined that some liquid polyesters can also cause an undesired anal leakage effect. This can be corrected by choosing polyesters of the preferred rheology or by adding certain agents to the polyester/vitamin compositions to avoid this undesired effect. (See U.S. Pat. Nos. 4,005,196 and 4,005,195.)

The following references are relevant to the present invention.

U.S. Pat. No. 3,600,186 (1971) to Mattson and Volpenhein discloses low-calorie food compositions containing polyol polyesters of the general type employed herein, and their use in combination with hardstocks which are fatty acid sources.

U.S. Pat. No. 3,954,976 of Mattson and Volpenhein, entitled "Pharmaceutical Compositions for Inhibiting Absorption of Cholesterol," discloses and claims sugar polyesters of the general type employed herein for the treatment and/or prevention of hypercholesterolemia. A variety of optional carriers are mentioned, including the fatty acid, stearic acid.

U.S. Pat. No. 1,656,474 (1928) to Dubin discloses edible fat compositions consisting of ethyl and glycerol esters of odd-chain fatty acids in combination with fat-soluble vitamins.

Mattson and Nole, *The Journal of Nutrition*, Vol 102, No. 9, Sept. 1972, at pages 1171–1175, report on the lack of absorbability of sugar polyesters of the general type employed herein in rats. The rats were fed water-soluble vitamins in the diet and given one drop of fat-soluble vitamins per week.

U.S. Pat. No. 2,962,419 (1960) to Minich relates to neopentyl fatty esters, their use as fat substitutes, and their use with "vitamins", among other things.

U.S. Pat. No. 3,160,565 (1964) to H. E. Duell relates to sugar mono-, di- and tri-esters and their use as carriers for various orally administered medicinals, including the B vitamins.

U.S. Pat. No. 3,849,554 (1974) to Winitz discloses means for reducing blood serum cholesterol by ingesting diets comprising a fatty acid source, said diets being low in sucrose.

U.S. Pat. No. 2,893,990 (1959) to Hass, et al., discloses fatty acid mono- and di-esters of sucrose which aid in the absorption of fat from the digestive tract.

U.S. Pat. No. 3,158,490 (1964) to Baur and Lutton discloses non-cloudy salad oils containing esters of disaccharides in which there are not more than five unesterified hydroxyl groups. See also U.S. Pat. Nos. 3,059,009 (1962) and 3,059,010 (1962) to Schmid and Baur.

U.S. Pat. No. 2,997,492 (1961) to Martin is directed to a method of making partial fatty acid esters of hexitols. U.S. Pat. No. 2,997,491 (1961) to Huber is directed to the synthesis of partial fatty esters of inositol. The general methods of synthesis disclosed in these patents can be used to prepare the liquid polyesters herein. Preferred methods of synthesis are fully disclosed hereinafter.

SUMMARY OF THE INVENTION

Administration of anti-ulcerative amounts of a composition comprising a liquid or solid polyester of the type described herein to persons afflicted with duodenal ulcers is an effective means of controlling the ulcer. The consumption of diets containing the specific non-digestible low-calorie fat materials has been shown in animal studies to reduce the size and severity of duodenal ulcers. In animal studies using rats with cysteamine-induced duodenal ulcers, the rats showed a 17% to 39% decrease in severity of duodenal ulcers and a 35% to 57% decrease in ulcer size. The rat's diet which contained approximately 10% of the described polyester, consuming (approximately 500 mg to 2000 mg per day) as total low-calorie fat material.

The present invention encompasses the use of liquid or solid, non-absorbable, non-digestible, polyol fatty acid polyester of the type described hereinafter to treat duodenal ulcers. The composition can also contain other materials. The compositions can be used as fat substitutes in foods or can be self-administered to accelerate healing of duodenal ulcers. Such compositions also find use as diet aids for the ulcerative individual.

The present invention also encompasses non-anal leakage pharmaceutical compositions in effective unit dosage amounts for reducing size and severity of duodenal ulcers without altering the body's fat-soluble vitamin status. These compositions contain from about 1 gram to about 5 grams of solid or liquid polyesters as described herein.

It is an object of the present invention to provide a low-calorie fat material for use in low-calorie food compositions or theorapeutic compositions and as a method for accelerating the healing of duodenal ulcers.

These and other objects of the invention will be made clear by the disclosure herein.

DETAILED DESCRIPTION OF THE INVENTION

Definitions

By anti-ulcerative is meant that the administration of these low-calorie fat materials accelerates healing time of duodenal ulcers.

By "low-calorie fat materials" is meant edible materials which can replace triglyceride fats or other oils in the human diet. These materials provide the benefits of triglyceride fats and oils, i.e., lubricity and flavors.

By "wholly nondigestible" is meant that substantially all of the material is not digested by the body. It passes through the digestive system substantially the same as when it was ingested. The term "partially nondigestible" means that at least about 30% of the material is not digested. Preferably at least about 70% of the material is not digested.

By "liquid/solid stability" as used herein is meant that the liquid portion of the material does not readily separate from the solid portion at body temperature, i.e., the material appears to be a solid even though up to about 95% of it is liquid. Liquid/solid stability is measured by centrifuging a sample of the material at 60,000 rpm for one hour at 100° F. (37.8° C.). Liquid/solid stability is defined as: 100% minus percentage of the material that separated as a liquid after centrifuging.

By "pharmaceutically effective amount" is meant a dosage effective to accelerate healing or lessen the severity of duodenal ulcers in animals and humans. Significant improvement in the rate of duodenal ulcer healing was observed in rats consuming a diet containing 10% of the polyester material. This corresponds to approximately 50 g/day of the material for humans, on a weight percent of average diet solids basis.

Low-Calorie Fat Materials

There are low-calorie fat materials with a rheology such that they have little or no anal leakage. The rheology of such low-calorie fat materials at body temperature (98.6° F., 37° C.) is of concern because they must be stable and viscous at body temperature to eliminate anal leakage. The measurements herein are done at 100° F. (37.8° C.) as a matter of convenience and for easier calibration of instruments.

Some liquid polyesters can exhibit an anal leakage problem. However, by combining liquid polyester compositions with an anti-anal leakage agent, especially a $C_{12}$ or higher, saturated fatty acid, or edible source which provides such fatty acids in the gut, this undesired anal leakage effect is prevented. See U.S. Pat. No. 4,005,195 for specific compositions, the disclosure of which is incorporated by reference.

The most preferred compositions herein do not exhibit this problem.

The low-calorie fat materials useful in the present invention can be any of a variety of edible, wholly or partially nondigestible compounds. The low-calorie fat material preferably has a complete melting point higher than about 98.6° F. (37° C.). Preferably, the fat material is selected from the group consisting of polyol fatty acid polyesters and polycarboxylic acids esterified with fatty alcohols, and mixtures thereof. Preferred polyol fatty acid polyesters are sugar fatty acid polyesters, sugar alcohol fatty acid polyesters, and polyglycerol fatty acid polyesters, and mixtures thereof. More preferably, the fat material is selected from the group consisting of sugar fatty acid polyesters and sugar alcohol fatty acid polyesters, and mixtures thereof, the sugars and sugar alcohols containing from 4 to 8 hydroxyl groups.

Sugar or sugar alcohol fatty acid polyesters comprise sugars or sugar alcohols, and fatty acids. The term "sugar" is used herein in its conventional sense as generic to mono-and disaccharides. The term "sugar alcohol" is also used in its conventional sense as generic to the reduction product of sugars wherein the aldehyde or ketone group has been reduced to an alcohol. The fatty acid ester compounds are prepared by reacting a monosaccharide, disaccharide or sugar alcohol with fatty acids as discussed below.

Examples of suitable monosaccharides are those containing 4 hydroxyl groups such as xylose, arabinose, and ribose; the sugar alcohol derived from xylose, i.e., xylitol with 5 hydroxyl groups, is also suitable. The monosaccharide erythrose is not suitable for the practice of this invention since it only contains 3 hydroxyl groups; however, the sugar alcohol derived from erythrose, i.e. erythritol, contains 4 hydroxyl groups and is thus suitable. Among 5 hydroxyl-containing monosaccharides that are suitable for use herein are glucose, mannose, galactose, fructose, and sorbose. A sugar alcohol derived from sucrose, glucose, or sorbose, e.g., sorbitol, contains 6 hydroxyl groups and is also suitable as the alcohol moiety of the fatty acid ester compound. Examples of suitable disaccharides are maltose, lactose, and sucrose, all of which contain 8 hydroxyl groups.

In preparing sugar or sugar alcohol fatty acid polyesters of the present invention a sugar or sugar alcohol compound such as those identified above must be esterified with a mixture of fatty acids having from about 8 to about 22 carbon atoms. Examples of such fatty acids are caprylic, capric, lauric, myristic, myristoleic, palmitic, palmitoleic, stearic, oleic, ricinoleic, linoleic, linolenic, eleostearic, arachidic, behenic, and erucic. The fatty acids can be derived from suitable naturally occurring or synthetic fatty acids and can be saturated or unsaturated, including positional and geometric isomers. The fat materials of this invention are mixed esters of fatty acids, rather than esters of a single type of fatty acid.

Fatty acids per se or naturally occurring fats and oils can serve as the source for the fatty acid component in the sugar or sugar alcohol fatty acid ester. For example, rapeseed oil provides a good source for $C_{22}$ fatty acid. $C_{16}$–$C_{18}$ fatty acid can be provided by tallow, soybean oil, or cottonseed oil. Shorter-chain fatty acids can be provided by coconut, palm kernel, or babassu oils. Corn oil, lard, olive oil, palm oil, peanut oil, safflower seed oil, sesame seed oil, and sunflower seed oil, are examples of other natural oils which can serve as the source of the fatty acid component.

The sugar or sugar-alcohol fatty acid polyesters suitable for use herein can be prepared by a variety of methods well known to those skilled in the art. These method include: transesterification of the sugar or sugar alcohol with methyl, ethyl or glycerol fatty acid esters using a variety of catalysts; acylation of the sugar or sugar alcohol with a fatty acid chloride; acylation of the sugar or sugar alcohol with a fatty acid anhydride; and acylation of the sugar or sugar alcohol with a fatty acid, per se. As an example, the preparation of sugar and sugar alcohol fatty acid esters is described in U.S. Pat. No. 2,831,854.

A characterizing feature of the sugar or sugar-alcohol fatty acid polyesters useful in this invention is that they predominantly contain at least 4 fatty acid polyester groups. Sugar or sugar-alcohol fatty acid polyester compounds that contain 3 or less fatty acid ester groups are digested in the intestinal tract much in the manner as ordinary triglyceride fats, but sugar or sugar-alcohol fatty acid polyester compounds that contain four or more fatty acid ester groups are digested to a lesser extent and thus have the desired low-calorie properties for use in this invention.

Highly preferred low-calorie fat materials according to this invention are sucrose fatty acid polyesters. Preferred sucrose fatty acid polyesters have the majority of their hydroxyl groups esterified with fatty acids. Preferably at least about 85%, and most preferably at least about 95%, of the sucrose fatty acid polyesters are selected from the group consisting of octaesters, heptaesters, hexaesters, and mixtures thereof. Preferably, no more than about 35% of the esters are hexaesters or heptaesters, and at least about 60% of the sucrose fatty acid polyesters are octaesters. Most preferably, at least about 70% of the polyesters are octaesters.

In order to provide the required physical properties, the preferred sucrose fatty acid polyesters which will not require anti-anal leakage agents are preferably esterified with particular kinds of fatty acids. Preferably, at least about 80%, and most preferably at least about 90%, of the fatty acids are selected from the group consisting of mixtures of palmitic, stearic, oleic, linoleic, and behenic acids.

More specifically, the following is a preferred fatty acid composition: from about 9% to about 12% palmitic; from about 35% to about 53% stearic; from about 19% to about 43% oleic; from about 2% to about 17% linoleic; from about 0% to about 2% linolenic; from about 0% to about 2% arachidic; from about 0% to about 10% behenic; and from about 0% to about 2% erucic.

The following fatty acid composition is most preferred: from about 9% to about 12% palmitic; from about 42% to about 53% stearic; from about 19% to about 39% oleic; from about 2% to about 17% linoleic; from about 0% to about 2% linolenic; from about 0% to about 2% arachidic; from about 0% to about 10% behenic; and from about 0% to about 2% erucic.

Preferred compositions for treating ulcers comprise an edible, wholly or partially nondigestible low-calorie fat material having physical chemical properties such that it has a non-Newtonian pseudoplastic rheology at 100° F. (37.8° C.). In particular, at 100° F. (37.8° C.) the fat material has: (a) a viscosity of at least about 2.5 poise at a shear rate of 800 seconds$^{-1}$, a viscosity of at least about 4.0 poise at a shear rate of 100 seconds$^{-1}$, and a viscosity of at least about 15.0 poise at a shear rate of 10 seconds$^{-1}$; (b) a yield point of at least about 2,500 dynes/cm$^2$; (c) a thixotropic area of at least about 0.20×10$^6$ dynes/cm$^2$-sec.; and (d) a liquid/solid stability of at least about 50%.

Viscosity, yield point, and thixotropic area are well-known rheological properties, and can be measured as later described.

At 100° F. (37.8° C.) the low-calorie fat materials preferred for this invention have a viscosity of at least about 5 poise at a shear rate of 800 seconds$^{-1}$, a viscosity of at least about 20 poise at a shear rate of 100 seconds$^{-1}$, and a viscosity of at least about 200 poise at a shear rate of 10 seconds$^{-1}$. The preferred yield point of the compositions is at least about 5,000 dynes/cm$^2$, and the preferred thixotropic area is at least about 0.75×10$^6$ dynes/cm$^2$-sec. Preferably, the compositions have a liquid/solid stability of at least about 90%.

Most preferably, at 100° F. (37.8° C.) the low-calorie fat materials have a viscosity of at least about 8 poise at a shear rate of 800 seconds$^{-1}$, a viscosity of at least about 30 poise at a shear rate of 100 seconds$^{-1}$, and a viscosity of at least about 400 poise at a shear rate of 10 seconds$^{-1}$. The most preferred yield point of the compositions is at least about 15,000 dynes/cm$^2$, and the most preferred thixotropic area is at least about 1.00×10$^6$ dynes/cm$^2$-sec.

The preferred upper limit of the viscosity of the fat materials of this invention is about 1×10$^5$ poise at a shear rate of 10 seconds$^{-1}$, and about 1,000 poise at a shear rate of 100 seconds$^{-1}$. The fat materials must have pseudoplastic flow properties as defined herein.

Iodine Value is a measure of the degree of unsaturation of fatty acids. The preferred low-calorie fat materials of this invention preferably have an Iodine Value of from about 36 to about 55.

The Solid Fat Content value (SFC) provides a reasonable approximation of the percent by weight solids of a particular fatty material at a given temperature. The present low-calorie fat material preferably has a Solid Fat Content at 100° F. (37.8° C.) of at least about 5%. Most preferably, the Solid Fat Content at 100° F. (37.8° C.) is at least about 10%. The solid fat content can be 35% or even higher.

Polyglycerol fatty acid polyesters can also be low-calorie fat materials of the present invention. Polyglycerol is prepared by the polymerization of glycerine in the presence of either acid or base. The polyglycerols can contain from 2 to 20 glycerol moieties. Preferably, the polyglycerols will be those having from 2 to 15 glycerol moieties.

The polyglycerol compounds can be made by any synthetic method. See, for example, U.S. Pat. No. 3,968,169 to Seiden and Martin (1976). Esterification of the polyglycerols can also be done by any method known to the art, providing the resulting polyglycerol esters have the rheological properties required of the present invention.

Animal studies have now shown polyglycerol esters with the following rheological properties to be very effective at eliminating anal leakage: (a) a viscosity of 3.13 poise at a shear rate of 800 seconds$^{-1}$, a viscosity of 5.18 poise at a shear rate of 100 seconds$^{-1}$, and a viscosity of 32.43 poise at a shear rate of 10 seconds$^{-1}$; (b) a thixotropic area of 0.246×10$^6$ dynes/cm$^2$-sec.; and (c) a liquid/solid stability of 53.45%.

The "polycarboxylic acids esterified with fatty alcohols" are tricarboxylic and tetracarboxylic acids and higher. The polycarboxylic acids can be partially or wholly esterified with fatty alcohols. At least three fatty alcohol groups must be esterified to a polycarboxylic acid to make it partially nondigestible.

Food Compositions

The low-calorie fat materials of the present invention can be used as a partial or total replacement for normal triglyceride fat in any fat-containing food composition to provide low-calorie benefits and to treat duodenal ulcers. Very low-calorie and thus highly desirable food compositions of the invention are obtained when the fat comprises up to about 100% of the fat materials of this invention, and from 25% to 100% of the calories. These foods can then be consumed in pharmaceutically effective amounts.

The present low-calorie fat materials, and particularly sucrose polyesters, can be incorporated into a wide variety of food and beverage products. For example, the fat materials can be used in the production of baked goods in any form, such as mixes, shelf-stable baked goods, and frozen baked goods. Possible applications include, but are not limited to, cakes, brownies, muffins, bar cookies, wafers, biscuits, pastries, pies, pie crusts, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other baked good uses include breads and rolls, crackers, pretzels, pancakes, waffles, ice cream cones and cups, yeast-raised baked goods, pizzas and pizza crusts, baked farinaceous snack foods, and other baked salted snacks.

In addition to their uses in baked goods, the low-calorie fat materials can be used alone or in combination with other regular, reduced-calorie or zero-calorie fats to make shortening and oil products. The other fats can be synthetic or derived from animal or vegetable sources, or combinations of these. Shortening and oil products include, but are not limited to, shortenings, margarines, spreads, butter blends, lards, cooking and frying oils, salad oils, popcorn oils, salad dressings, mayonnaise, and other edible oils.

Other materials which can be added to the foods or doses include vitamins and minerals. Fat-soluble vitamins include vitamin A, vitamin D, vitamin E, and vitamin K. The amount of the fat-soluble vitamins employed herein to fortify the present low-calorie fat materials can vary. If desired, the fat materials can be fortified with a recommended daily allowance (RDA), or increment or multiple of an RDA, of any of the fat-soluble vitamins or combinations thereof.

Vitamins that are nonsoluble in fat can similarly be included in the present low-calorie fat materials. Among these vitamins are the vitamin B-complex vitamins and vitamin C. The minerals include the wide variety of minerals known to be useful in the diet, such as calcium, magnesium, iron and zinc. Any combination of vitamins and minerals can be used in the present low-calorie fat materials.

The present olow-calorid fat materials aree particulay useful in combination with particular classes of food and beverage ingredients. For example, an extra calorie reduction benefit is achieved when the fat materials are used with noncaloric or reduced-calorie sweeteners alone or in combination with bulking agents. Noncaloric or reduced-calorie sweeteners include, but are not limited to, aspartame; saccharin; alitame, thaumatin; dihydrochalcones; cyclamates; steviosides; glycyrrhizins, synthetic alkoxy aromatics, such as Dulcin and P-4000; sucrolose; suosan; miraculin; monellin; sorbitol; xylitol; talin; cyclohexylsulfamates; substituted imidazolines; synthetic sulfamic acids such as acesulfame, acesulfam-K and n-substituted sulfamic acids; oximes such as perilartine; rebaudioside-A; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates.

The low-calorie fat materials can be used in combination with other noncaloric or reduced calorie fats, such as branched-chain fatty acid triglycerides, triglycerol ethers, polycarboxylic acid esters, sucrose polyethers, neopentyl alcohol esters, silicone oils/siloxanes, and dicarboxylic acid esters. Other partial fat replacements useful in combination with the fat materials are medium-chain triglycerides, highly esterified polyglycerol esters, acetin fats, plant sterol esters, polyoxyethylene esters, jojoba esters, mono/diglycerides of fatty acids, and mono/diglycerides of short-chain dibasic acids.

Bulking or bodying agents are useful in combination with the low-calorie fat materials in many food compositions. The bulking agents can be nondigestible carbohydrates, for example, polydextrose and cellulose or cellulose derivatives, such as carboxymethylcellulose, carboxyethylcellulose, hydroxypropylcellulose, methylcellulose and microcrystalline cellulose. Other suitable bulking agents include gums (hydrocolloids), starches, dextrins, fermented whey, tofu, maltodextrins, polyols, including sugar alcohols, e.g. sorbitol and mannitol, and carbohydrates, e.g. lactose.

Similarly, food and beverage compositions can be made that combine the present low-calorie fat materials with dietary fibers to achieve the combined benefits of each. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for examples, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

These dietary fibers may be in a crude or purified form. The dietary fiber used may be of a single type (e.g. cellulose), a composite dietary fiber (e.g. citrus albedo fiber containing cellulose and pectin), or some combination of fibers (e.g. cellulose and a gum). The fibers can be processed by methods known to the art.

Of course, judgement should be exercised to make use of appropriate low-calorie fat materials and combinations of the fat materials with other food ingredients. For example, a combination of sweetener and fat material would not be used where the specific benefits of the two are not desired. The fat materials and fat material/ingredient combinations are used where appropriate, and in the proper amounts.

Therapeutic Treatment

In therapeutic regimens the dosage of the compositions herein can vary with the severity of the ulcerative condition and the duration of the treatment. Individual doses can range up to about 60 gm per day, preferably from about 10 gm to about 50 gm per day in up to six doses, preferably three doses, being given daily, most preferably at meal times. The doses can be administered orally in any suitable unit dosage form such as pills, tablets, and capsules. Preferred are capsules made from gelatin. The doses can also be administered as part of a controlled dietary regimen, e.g., as a synthetic salad oil or cooking oil or fat, or foods as herein described.

The pharmaceutical compositions herein can comprise the polyester agent alone, or in combination with any desired, non-interfering pharmaceutical carrier. As used herein, the term "pharmaceutical carrier" means a solid or liquid filler, diluent or encapsulating substance. Some examples of the substances which can serve as pharmaceutical carriers are sugars such as lactose, glucose and sucrose; starches such as corn starch and potato starch; cellulose and its derivatives such as sodium carboxymethylcellulose, ethylcellulose, cellulose acetate; powdered tragacanth; malt; gelatin; talc; oils such as peanut oil, cottonseed oil, sesame oil, olive oil, corn oil and soybean oil; polyols such as propylene glycol, glycerin, sorbitol, mannitol, and polyethylene glycol; agar; alginic acid; pyrogen-free water; isotonic saline; ethyl alcohol and phosphate buffer solutions, as well as other non-toxic compatible substances used in pharmaceutical formulations. Wetting agents and lubricants such as sodium lauryl sulfate, as well as coloring agents, flavoring agents and preservatives can also be present in the compositions, according to the desires of the formulator.

The pharmaceutical carriers of the foregoing type can optionally be employed in conjunction with the liquid polyesters herein to provide a practical size to dosage relationship, composition forms which can be easily ingested, and means for providing accurate unit dosages in a convenient form. The pharmaceutical carrier usually will comprise from about 5% to about 50% by weight of the total pharmaceutical composition.

ANALYTICAL METHODS

I. RHEOLOGY MEASUREMENTS

A. Sample Preparation

The low-calorie fat material is melted in a microwave oven at about 150° F. (66° C.) to about 170° F. (77° C.). This takes approximately 2 minutes. The melted fat material is held at 100° F.±5° F. (37.8° C.±3° C.), and a 3 gram sample is weighed into a Solo ® plastic souffle cup. The sample is then allowed to recrystallize at 100° F.±5° F. (37.8° C.±3° C.) for 24 hours. After the 24 hour time period has elapsed, the sample is taken to the viscometer in an insulated cup and the viscosity is measured.

B. Ferranti-Shirley Viscometer Operation Procedure

A Ferranti-Shirley (manufactured in New York) viscometer is used for the viscosity, yield point, and thixotropic area measurements. A cone is put into place, and the viscometer temperature is adjusted to 100° F. (37.8° C.). The chart recorder is calibrated, and the gap between the cone and plate is set. The cone speed is checked, and the cone and plate temperatures are equilibrated to 100° F. (37.8° C.). The panel controls are set. Sufficient sample is placed between the plate and the cone so that the gap is completely filled. The temperature is allowed to stabilize at 100° F. (37.8° C.) for about 30 seconds, and then the cone rotation and recording are started. A rheogram for the fat material is recorded and analyzed to determine the viscosity, yield point, and thixotropic area. The viscometer is programmed to ramp up in shear rate continuously from 0 seconds$^{-1}$ to 800 seconds$^{-1}$ in 120 seconds, then ramp down in shear rate from 800 seconds$^{-1}$ to 0 seconds$^{-1}$ in 120 seconds. Viscosity is measured at shear rates of 800 seconds$^{-1}$, 100 seconds$^{-1}$, and 10 seconds$^{-1}$ on the decreasing shear rate ramp.

II. LIQUID/SOLID STABILITY MEASUREMENT

The sample is heated until it completely melts and is thoroughly mixed. The sample is then poured into centrifuge tubes at 100° F.±5° F. The samples then are allowed to recrystallize for 24 hours at 100° F.±5° F. The samples are then centrifuged at 60,000 rpm for one hour at 37° C. The maximum on the samples is 48,000 g's. The percent liquid separated is then measured by comparing the relative heights of the liquid and solid phases.

III. SOLID FAT CONTENT MEASUREMENT

Before determining SFC values, the fat material sample is heated to a temperature of 158° F. (70° C.) or higher for at least 0.5 hours or until the sample is completely melted. The melted sample is then tempered at a temperature of 40° F. (4.4° C.) for at least 72 hours. After tempering, the SFC value of the fat material at a temperature of 100° F. (37.8° C.) is determined by pulsed nuclear magnetic resonance (PNMR). The method for determining SFC values of a fat by PNMR is described in Madison and Hill, *J. Amer. Oil. Chem. Soc.*, Vol. 55 (1978), pp. 328-31 (herein incorporated by reference).

The following examples exemplify the invention but are not intended to be limiting.

EXAMPLE I

The compositions listed in Table 1 are fed to female Sprague-Dawley rats at a rate of 10% of their diets. The remainder of the diet consists of Purina Rodent Chow number 5002. The control diet contains 10% triglyceride consisting of a blend of soybean oil and hydrogenated palm oil. These rats have duodenal ulcers which are induced by administration of cysteamine hydrochloride. After three days, the severity of the duodenal ulcers is assessed. Those with ulcers are divided into groups based on ulcer severity. These groups have equal severity of ulcers. The groups are fed either an experimental or control diet ad libitum for 21 days. After 18 days of treatment, the rats show a 17% to 39% decrease in severity of the ulcers and a 35% to 57% decrease in ulcer size, relative to duodenal ulcers in animals consuming the control diet.

EXAMPLE II

Gelatin capsules are prepared containing 1 gm sucrose polyesters, having at least 70% octaesters and being esterified with the following fatty acids: palmitic, stearic, oleic, linoleic and behenic acids.

EXAMPLE III

Patients are fed a diet in which from 10% to 100% of the fat is replaced with a sucrose polyesters of the type in Table I up to a level of 50 gm/day. These patients show improvement in the size and severity of their duodenal ulcers.

TABLE I

| Fatty Acid Composition | Sucrose Polyester Composition | | Liquid Sucrose Polyester |
|---|---|---|---|
| | Example 1 | Example 2 | |
| | % | % | % |
| Others | 4.1 | 2.6 | 3.4 |
| $C_{16}$ | 11.8 | 9.4 | 8.6 |
| $C_{18}$ | 43.0 | 51.8 | 5.7 |
| $C_{18:1}$ | 37.3 | 20.4 | 45.6 |
| $C_{18:2}$ | 2.6 | 15.8 | 31.7 |
| $C_{18:3}$ | 0.6 | 0.0 | 0.4 |
| $C_{20}$ | 0.6 | 0.0 | 0.6 |
| $C_{22}$ | 0.0 | 0.0 | 0.0 |

TABLE I-continued

| Sucrose Polyester Composition | | | |
|---|---|---|---|
| | Example 1 | Example 2 | Liquid Sucrose Polyester |
| I.V. | 38.2 | 47.6 | 62.6 |
| Ester Distribution | % | % | % |
| Octa | 94.5 | 79.0 | 71.1 |
| Hepta | 5.6 | 19.2 | 24.0 |
| Hexa | 0.0 | 1.8 | 4.9 |
| Penta | 0.1 | 0.1 | 0.1 |
| Penta | 0.1 | 0.1 | 0.1 |
| SFC Profile | % | % | % |
| 50 F. | 67.6 | 64.3 | 0 |
| 70 F. | 55.2 | 53.6 | 0 |
| 80 F. | 44.2 | 43.0 | 0 |
| 92 F. | 23.3 | 21.1 | 0 |
| 105 F. | 5.2 | 2.7 | 0 |
| 98.6 F. | 14.3 | 11.9 | 0 |
| DSC Behavior | C. | C. | C. |
| Complete Melt Point | 38.9 | 42.5 | −20.0 |
| Maximum Melt Point | 36.0 | 39.4 | −35.0 |
| Heat of Fusion | 14.8 | 11.7 | 10.6 |

What is claimed is:

1. A method for treating duodenal ulcers by treating the patient with pharmaceutically effective amounts of wholly or partially non-digestible low-calorie fat material comprising polyol fatty acid polyesters.

2. A method according to claim 1 wherein the polyol polyester has at 100° F.:
   (a) a viscosity of at least about 2.5 poise at a shear rate of 800 seconds$^{-1}$, a viscosity of at least about 4.0 poise at a shear rate of 100 seconds$^{-1}$, and a viscosity of at least about 15.0 poise at a shear rate of 10 seconds$^{-1}$;
   (b) a yield point of at least about 2,500 dynes/cm$^2$;
   (c) a thixotropic area of at least about 0.20×10$^6$ dynes/cm$^2$-sec.; and
   (d) a liquid/solid stability of at least about 50%.

3. A method according to claim 2 wherein the fat material is selected from the group consisting of sugar fatty acid polyesters, sugar alcohol fatty acid polyester, and polyglycerol fatty acid polyesters, and mixtures thereof.

4. A method according to claim 3 wherein the sugar fatty acid polyesters and sugar alcohol fatty acid polyesters are selected from the group consisting of sugar fatty acid polyesters and sugar alcohol fatty acid polyesters wherein the sugars and sugar alcohols contain from 4 to 8 hydroxyl groups and each fatty acid group has from about 8 to about 22 carbon atoms.

5. A method according to claim 4 wherein the sugar fatty acid polyester comprises sucrose fatty acid esters.

6. A method according to claim 5 wherein the sugar fatty acid polyester comprises sucrose fatty acid esters wherein at least about 60% of the polyesters are octaesters.

7. A method according to claim 6 wherein the sugar fatty acid polyester comprises sucrose fatty acid esters wherein at least about 80% of the fatty acids are selected form the group consisting of mixtures of palmitic, stearic, oleic, linoleic and behenic acids.

8. A method according to claim 7 wherein the sugar fatty acid polyester comprises sucrose fatty acid esters wherein at least about 90% of the fatty acids are selected form the group consisting of mixtures of palmitic, stearic, oleic, linoleic and behenic acids.

9. A method according to claim 8 wherein the sugar fatty acid polyester comprises sucrose fatty acid esters having a yield point of at least about 5,000 dynes/cm$^2$.

10. A method according to claim 9 wherein the sugar fatty acid polyester comprises sucrose fatty acid esters having a liquid/solid stability of at least about 90%.

11. A method according to claim 10 wherein the sugar fatty acid polyester comprises sucrose fatty acid esters having an Iodine Value of from about 36 to about 55.

12. A method according to claim 10 wherein the sugar fatty acid polyester comprises sucrose fatty acid esters having a solid fat content at 100° F. of at least about 5%.

13. A method according to claim 12 wherein the sugar fatty acid polyester comprises sucrose fatty acid esters having a complete melting point higher than about 98.6° F.

14. A method according to claim 3 wherein said low-calorie fat material is a food composition comprising non-fat ingredients and fat ingredients.

15. A method according to claim 14 wherein the fat material is selected from the group consisting of sugar fatty acid polyesters, sugar alcohol fatty acid polyester, and polyglycerol fatty acid polyesters, and mixtures thereof.

16. A method according to claim 15 wherein the sugar fatty acid polyesters and sugar alcohol fatty acid polyesters are selected from the group consisting of sugar fatty acid polyesters and sugar alcohol fatty acid polyesters wherein the sugars and sugar alcohols contain from 4 to 8 hydroxyl groups and each fatty acid group has from about 8 to about 22 carbon atoms.

17. A method according to claim 16 wherein the sugar fatty acid polyester comprises sucrose fatty acid esters.

18. A method according to claim 17 wherein the sugar fatty acid polyester comprises sucrose fatty acid esters wherein at least about 60% of the polyesters are octaesters.

19. A method according to claim 18 wherein the sugar fatty acid polyester comprises sucrose fatty acid esters wherein at least about 80% of the fatty acids are selected from the group consisting of mixtures of palmitic, stearic, oleic, linoleic and behenic acids.

20. A method according to claim 19 wherein the sugar fatty acid polyester comprises sucrose fatty acid esters wherein at least about 90% of the fatty acids are selected from the group consisting of mixtures of palmitic, stearic, oleic, linoleic and behenic acids.

21. A method according to claim 3 wherein said low-calorie fat material is in a food composition comprising non-fat ingredients and fat ingredients and wherein said food is selected from the group consisting of margarine, ice cream, cheese, meat analogs, meat substitutes, pudding and baked goods.

22. A method according to claim 21 wherein the baked goods is cookies.

23. A method according to claim 1 wherein said low-calorie fat is administered in unit dosage form.

24. A method according to claim 23 wherein said unit dosage form comprises capsules which deliver approximately 50 g per day of said low-calorie fat materials in from 3 to 6 doses.

* * * * *